(12) United States Patent
Racz et al.

(10) Patent No.: US 10,768,139 B2
(45) Date of Patent: Sep. 8, 2020

(54) ELECTROCHEMICAL PROBE

(71) Applicant: The Francis Crick Institute Limited, London (GB)

(72) Inventors: Romeo-Robert Racz, London (GB); Mihaly Kollo, London (GB); Andreas Schaefer, London (GB)

(73) Assignee: The Francis Crick Institute Limited, London (GB)

( * ) Notice: Subject to any disclaimer, the term of this patent is extended or adjusted under 35 U.S.C. 154(b) by 456 days.

(21) Appl. No.: 15/259,435

(22) Filed: Sep. 8, 2016

(65) Prior Publication Data

US 2018/0067075 A1    Mar. 8, 2018

(51) Int. Cl.
| | | |
|---|---|---|
| *G01N 27/416* | (2006.01) | |
| *G01N 27/30* | (2006.01) | |
| *C25D 13/02* | (2006.01) | |
| *C25D 13/20* | (2006.01) | |
| *C25D 13/22* | (2006.01) | |
| *G01N 27/28* | (2006.01) | |
| *H01R 4/64* | (2006.01) | |
| *G01N 27/327* | (2006.01) | |

(52) U.S. Cl.
CPC .......... *G01N 27/416* (2013.01); *C25D 13/02* (2013.01); *C25D 13/20* (2013.01); *C25D 13/22* (2013.01); *G01N 27/283* (2013.01); *G01N 27/302* (2013.01); *H01R 4/64* (2013.01); *G01N 27/305* (2013.01); *G01N 27/3275* (2013.01)

(58) Field of Classification Search
CPC ... A61B 5/1468; A61B 5/1473; A61B 5/1486; A61B 5/14865; A61B 5/04001; A61B 5/04002; A61B 5/053; A61B 25/02; A61B 25/16; A61N 1/0428; A61N 1/0432; A61N 1/0452–0468; G01N 27/02; G01N 27/026; G01N 27/327; G01N 27/3275; G01N 27/333; G01N 27/403; G01N 27/302; G01N 27/04128; G01N 27/22
See application file for complete search history.

(56) References Cited

U.S. PATENT DOCUMENTS

| | | | |
|---|---|---|---|
| 2009/0248113 A1* | 10/2009 | Nimer | A61N 1/05 607/60 |
| 2011/0208031 A1* | 8/2011 | Wolfe | A61B 5/0478 600/378 |

(Continued)

OTHER PUBLICATIONS

Castagnola, Elisa, et al.; Smaller, softer, lower-impedance electrodes for human neuroprosthesis: a pragmatic approach; frontiers in Neuroengineering; vol. 7, article 8, pp. 1-17; Apr. 2014 (Year: 2014).*

(Continued)

*Primary Examiner* — Edward J. Schmiedel
(74) *Attorney, Agent, or Firm* — Nixon & Vanderhye P.C.

(57) ABSTRACT

An electrochemical probe comprises a wire bundle including two or more wire electrodes made of conducting material arranged alongside each other, and insulating material surrounding the electrodes. An impedance reducing layer of metal or metal oxide nano-structures is deposited on tips of the wire electrodes at a first end of the bundle. A functionalization layer is deposited on the impedance reducing layer at the first end of the bundle. Such a probe is particularly useful for electrochemical sensing applications such as neuronal scanning.

17 Claims, 12 Drawing Sheets

(56) References Cited

U.S. PATENT DOCUMENTS

| | | | | |
|---|---|---|---|---|
| 2011/0233075 | A1* | 9/2011 | Soleymani | G01N 33/5438 205/792 |
| 2014/0371564 | A1* | 12/2014 | Anikeeva | A61N 1/0551 600/377 |
| 2016/0128588 | A1 | 5/2016 | Melosh et al. | |

OTHER PUBLICATIONS

N.A. Alba et al, "In Vitro Electrochemical Analysis of a PEDOT/MWCNT Neural Electrode Coating" *Biosensors*, 2015, 5, Oct. 13, 2015, pp. 618-646.

C. Boehler et al, "Nanostructured platinum grass enables superior impedance reduction for neural microelectrodes" *Biomaterials*, 67, Jul. 21, 2015, pp. 346-353.

Ch. Broennimann et al, "Development of an Indium bump bond process for silicon pixel detectors at PSI" *Nuclear Instruments and Methods in Physics Research A*, May 26, 2006, pp. 303-308.

N.M. Carretero et al, "Enhanced Charge Capacity in Iridium Oxide-Graphene Oxide Hybrids" *Electrochimica Acta*, accepted Oct. 10, 2014, pp. 1-17.

I.G. Casella et al, "Anodic electrodeposition of iridium oxide particles on glassy carbon surfaces and their electrochemical/SEM/XPS characterization" *Journal of Electroanalytical Chemistry*, 736, Nov. 15, 2014, pp. 147-152.

E. Castagnola et al, "pHEMA Encapsulated PEDOT-PSS-CNT Microsphere Microelectrodes for Recording Single Unit Activity in the Brain" *Frontiers in Neuroscience*, 10, Apr. 18, 2016, pp. 1-14.

H. Charkhkar et al, "Chronic intracortical neural recordings using microelectrode arrays coated with PEDOT-TFB" *Acta Biomaterialia*, 32, Dec. 12, 2015, pp. 57-67.

T. Chung et al, "Electrode modifications to lower electrode impedance and improve neural signal recording sensitivity" *Journal of Neural Engineering*, 12 (2015), Sep. 23, 2015, pp. 1-14.

S.F. Cogan, "Neural Stimulation and Recording Electrodes" *Biomedical Engineering*, 10, Apr. 22, 2008, pp. 275-309.

J.E. Ferguson et al, "Creating low-impedance tetrodes by electroplating with additives" *Sensors and Actuators A: Physical*, 156, Oct. 9, 2009, pp. 388-393.

C.-C. Hu et al, "Cyclic voltammetric deposition of hydrous ruthenium oxide for electrochemical capacitors: effects of codepositing iridium oxide" *Electrochimica Acta*, 45 (2000) Jan. 24, 2000, pp. 2685-2696.

E.W. Keefer et al, "Carbon nanotube coating improves neuronal recordings" *Nature Nanotechnology*, vol. 3, Jul. 2008, pp. 434-439.

K. Kondo et al, "Copper Electrodeposition for Nanofabrication of Electronic Devices" *Nanostructure Science and Technology*, Nov. 20, 2013, pp. 1-282.

T.D.Y. Kozai et al, "Chronic in vivo evaluation of PEDOT/CNT for stable neural recordings" *IEEE Transactions on Biomedical Engineering*, 63(1), Jun. 15, 2015, pp. 1-9.

T.D.Y. Kozai et al, "Ultrasmall implantable composite microelectrodes with bioactive surfaces for chronic neural interfaces" *Nature Materials*, vol. 11, Nov. 11, 2012, pp. 1065-1073.

T.D.Y. Kozai et al, "Two-photon imaging of chronically implanted neural electrodes: Sealing methods and new insights" *Journal of Neuroscience Methods*, 258 (2016), available online Oct. 23, 2015, pp. 46-55.

D. Kuzum et al, "Transparent and flexible low noise graphene electrodes for simultaneous electrophysiology and neuroimaging" *Nature Communications*, 5, Oct. 20, 2014, pp. 1-10.

G. Lee et al, "Fabrication, structure and mechanical properties of indium nanopillars" *Acta Materialia* 58 (2010) available online Nov. 20, 2009, pp. 1361-1368.

Y. Lu et al, "Anodically electrodeposited iridium oxide films microelectrodes for neural microstimulation and recording" *Sensors and Actuators B: Chemical*, 137, Dec. 9, 2008, pp. 334-339.

S.C. Mailley et al, "Electrochemical and structural characterizations of electrodeposited iridium oxide thin-film electrodes applied to neurostimulating electrical signal" *Materials Science and Engineering*, 21 (2002), Sep. 2002, pp. 167-175.

R.D. Meyer et al, "Electrodeposited Iridium Oxide for Neural Stimulation and Recording Electrodes" *IEEE Transactions on Neural Systems and Rehabilitation Engineering*, vol. 9, No. 1, Mar. 2001, pp. 2-11.

D.-W. Park et al, "Graphene-based carbon-layered electrode array technology for neural imaging and optogenetic applications" *Nature Communications* 5, Oct. 20, 2014, pp. 1-11.

M.R. Pinnel et al, "Oxidation of Copper in Controlled Clean Air and Standard Laboratory Air at 50° C to 150° C"*Applications of Surface Science* vol. 2, Issue 4 (1979), May 1979, pp. 558-577.

R.P. Reed et al, "Tensile Strength and Ductility of Indium" *Materials Science and Engineering A*, 102, Feb. 11, 1988, pp. 227-236.

P. Steegstra et al, "Influence of oxidation state on the pH dependence of hydrous iridium oxide films" *Elecfrochimica Acta*, 76, May 15, 2012, pp. 26-33.

Yingtao Tian et al, "Electrodeposition of Indium for Bump Bonding" *Proceedings 2008 Electronic Components and Technology Conference* (ECTC 2008), Jun. 2008, pp. 2096-2100.

S. Venkatraman et al, "In Vitro and In Vivo Evaluation of PEDOT Microelectrodes for Neural Stimulation and Recording" *IEEE Transactions on Neural Systems and Rehabilitation Engineering*, vol. 19, No. 3, Jun. 2011, pp. 307-316.

M.T. Wang et al, "Barrier Properties of Very Thin Ta and TaN Layers Against Copper Diffusion" *Journal of the Electrochemical Society*, vol. 145, No. 7, Jul. 1998, pp. 2538-2545.

S.J. Wilks et al, "Poly(3,4-ethylenedioxythiophene) as micro-neural interface material for electrostimulation" *Frontiers in Neuroengineering*, vol. 2, Article 7, Jun. 9, 2009, pp. 1-8.

D.O. Wipf et al, "Microdisk electrodes: Part II. Fast-scan cyclic voltammetry with very small electrodes" *Journal of Electroanal. Chem.*, Mar. 30, 1989, pp. 15-25.

K. Yamanaka, "Anodically Electrodeposited Iridium Oxide Films (AEIROF) from Alkaline Solutions for Electrochromic Display Devices" *Japanese Journal of Applied Physics*, vol. 28, No. 4, Apr. 1989, pp. 632-637.

Canales Andres et al., "Multifunctional fibers for simultaneous optical, electrical and chemical interrogation of neural circuits in vivo", Nature Biotechnology, vol. 33, No. 3, pp. 277-284 (Mar. 2015).

Liao Yi-Fang et al., "A simple method for fabricating microwire tetrode with sufficient rigidity and integrity without a heat-fusing process", Journal of Neuroscience Methods, vol. 195, pp. 211-215 (2011).

* cited by examiner

ELECTROCHEMICAL PROBE

BACKGROUND

Technical Field

The present technique relates to the field of electrochemical probes.

Technical Background

Probes for sensing electrical and chemical events of biological systems can be useful for a range of applications, including electrochemical microscopy, a range of in vivo and/or in vitro bioelectrical event recordings, a range of determinations of biologically significant substance/substances (e.g. proteins, neurotransmitters, hydrogen peroxide, calcium, nitric oxide, DNA) or toxicologically relevant substance/substances (e.g.: heavy metals) and electrophysiological, extracellular and intracellular electrophysiological applications, tumor scanning and electrotherapy or cardiovascular scanning, for example.

SUMMARY

At least some examples provide an electrochemical probe comprising:
a wire bundle comprising a plurality of wire electrodes made of conducting material arranged alongside each other, and insulating material surrounding the electrodes; and
an impedance reducing layer of metal or metal oxide nano-structures deposited on tips of the wire electrodes at a first end of the wire bundle; and
a functionalization layer deposited on the impedance reducing layer at said first end of the bundle.

At least some examples provide an apparatus comprising:
an electrochemical probe as recited above; and
an integrated circuit comprising a plurality of contact portions to receive an electrode signal, and an amplifying portion to amplify the electrode signal received at the contact portions;
wherein connection layers of metal nano-structures on the tips of the wire electrodes at a second end of the wire bundle opposite the first end are in contact with corresponding contact portions of the integrated circuit.

At least some examples provide a method of manufacturing an electrochemical probe, comprising:
forming a wire bundle comprising a plurality of wire electrodes made of conducting material arranged alongside each other, and insulating material surrounding the electrodes; and
depositing an impedance reducing layer of metal or metal oxide nano-structures on tips of the wire electrodes at a first end of the wire bundle; and
depositing a functionalization layer on the impedance reducing layer at said first end of the bundle.

At least some examples provide an electrochemical probe comprising:
a wire bundle comprising a plurality of wire electrodes made of conducting material arranged alongside each other, and insulating material surrounding the electrodes; and
an impedance reducing layer of gold nano-structures deposited on tips of the wire electrodes at a first end of the wire bundle.

At least some examples provide a connector interface for coupling a conductive wire to a wire bundle comprising a plurality of wire electrodes, the connector interface comprising:

a casing comprising an aperture for receiving the wire bundle;
a conductive layer disposed within the aperture, wherein the conductive wire is coupled to the conductive disc and extends outwards through the casing; and
a carbon composite layer disposed within the aperture on the opposite side of the conductive layer to the side coupled to the conductive wire, wherein the carbon composite layer is closer to an opening of the aperture than the conductive layer.

Further aspects, features and advantages of the present technique will be apparent from the following description of examples, which is to be read in conjunction with the accompanying drawings.

DESCRIPTION OF EXAMPLES

Figure 1:
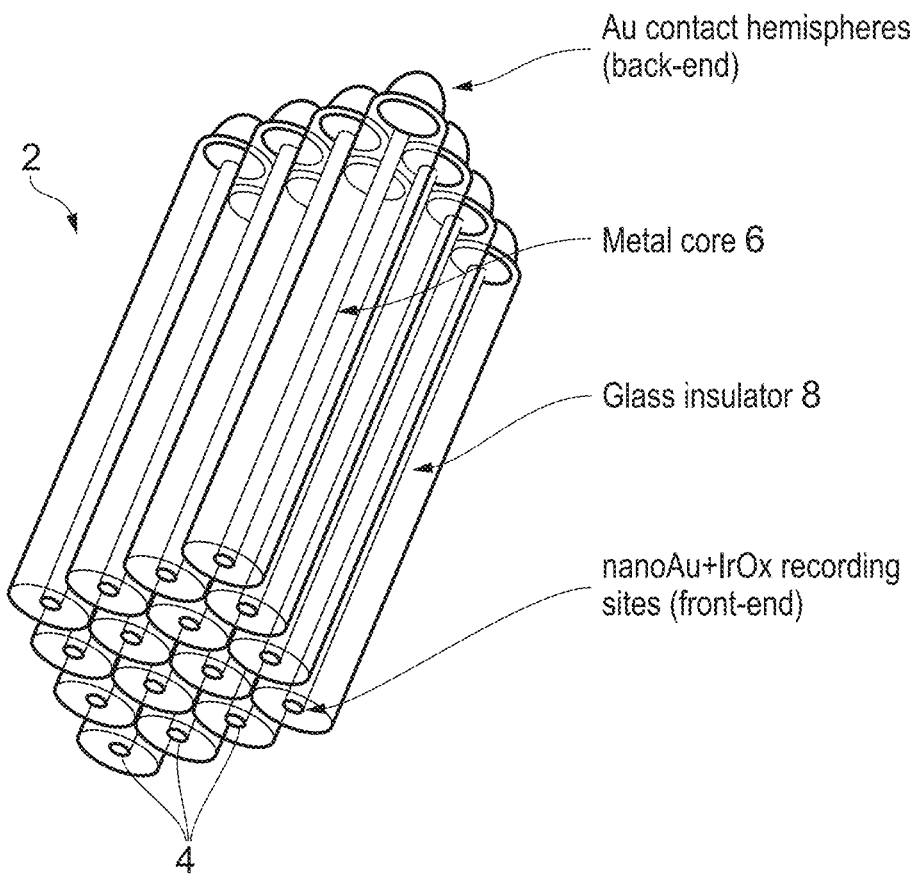
FIG. 1 schematically illustrates an example of an electrochemical probe comprising a bundle of wire electrodes surrounded in insulating material with impedance reducing layers made of gold nano-structures deposited on the tips of the wires at the front and back ends, and an iridium oxide functionalization layer deposited on the gold nano-structures at the front end of the wires.

FIG. 1 shows an example of an electrochemical probe 2. An electrochemical probe may be a probe for current and/or voltage measurements or injection in biological samples and a range of electrophysiological applications, or a probe for determination of the presence and/or quantity of one or more biologically and/or toxicologically significant substances in biological and/or liquid samples. The electrochemical probe 2 comprises a wire bundle including a number of wire electrodes 4 arranged alongside each other (for example the wire electrodes may be arranged parallel to each other or nearly parallel). The wires could be arranged in the bundle in a regular pattern (such as a square/rectangular lattice or stack arrangement, or a hexagonal packed arrangement), or in an irregular pattern. Each wire electrode 4 includes a core 6 made of a conducting material (e.g. a metal or alloy) surrounded by an insulating material 8. The electrodes 4 are ultramicroelectrodes (UMEs) having a diameter less than or equal to 25 μm. In this example the metal core 6 is made of gold, but other examples of conducting materials which could be used include copper, silver, gold, iron, platinum, lead or other metals, as well as crystalline or amorphous alloy compositions such as brass, bronze, platinum-iridium, lead-silver and magnetic alloys such as FeSiB. In this example, the insulating material 8 is glass, but other examples could use plastics or other insulators.

The probe 2 has a front end, which is the end of the probe for interfacing with the sensing target, and a back end, which is the end of the probe for transmitting the signals measured from the sensing target to the signal read out electronics or data processing equipment. At the front end, the wire electrodes 4 each have an impedance reducing layer of gold nano-structures deposited on the tips of the wire electrodes, and an iridium oxide (IrOx) functionalisation layer comprising a layer of iridium oxide nano-structures deposited on top of the gold nano-structures. At the back end, the tips of the wire electrodes have a connection layer for connecting to an electrical connector or the read out electronics. The connection layer in this example is also made of gold nano-structures, but the back end does not have the additional functionalization layer.

Figure 2:
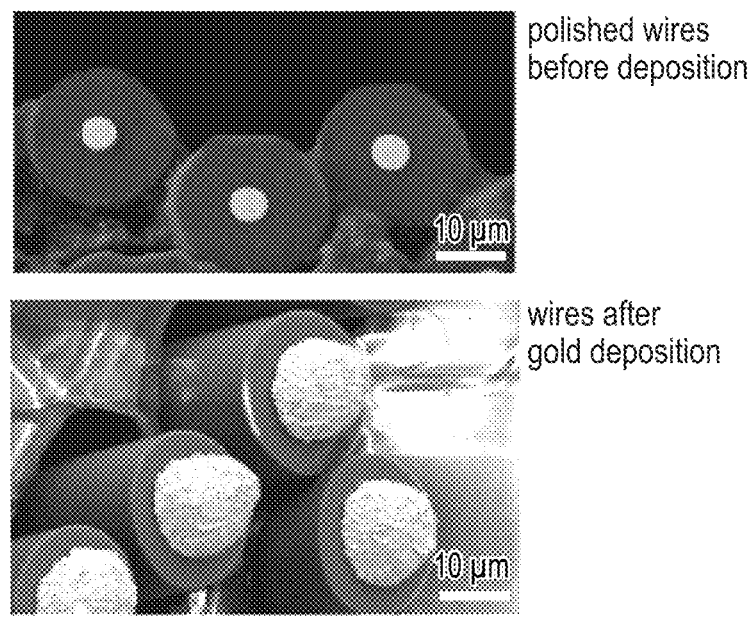
FIG. 2 shows an image of the wires before and after depositing the gold nano-structures.

FIG. 2 shows an image of the gold nano-structure hemispheres formed on the ends of the wires at the front end and the back end (before depositing the iridium oxide on top of the bumps at the front end). Each individual single crystal of the hemisphere may have a unit size in the nanometre scale, e.g. smaller than 100 or 50 nm for example. On the other hand, the overall hemisphere of nano-structures on the back-end may have a width at the micrometre scale, e.g. around 10-20 μm in this example, and on the front end the hemisphere may have a width not exceeding 20% of the wire core's diameter. As can be seen from FIG. 2, the hemisphere may extend over the insulating sheath of the wires as well as the core material on the back-end to facilitate contact with the integrated circuit providing the electronics for reading out signals from the probe. It will be appreciated that the gold-nanostructure layers formed at the front and back ends of the wire electrodes need not be perfectly hemispherical—in general any mound or bump formed on the tip of the wire electrodes may be sufficient.

Figure 3:
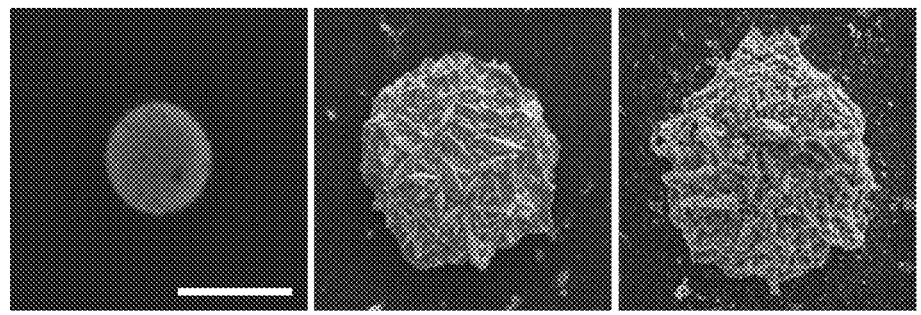
FIG. 3 shows images of the bare metal core wire, the tip of the wire after depositing the gold nano-structures and the tip after depositing the iridium oxide functionalization layer on the gold nano-structures.

FIG. 3 shows images illustrating the various layers deposited at the tips of the wire electrodes. The left hand image of FIG. 3 shows the bare polished metal core prior to depositing either of the layers onto the tip of the wire. The middle image shows the electrode after depositing the gold nanostructure layer. The layer of gold nanostructures has a flaky consistency, providing a large surface area for charge transfer which helps to reduce the impedance at the tips of the wire. The right hand image of FIG. 3 shows an image of the wire electrode after depositing the iridium oxide layer on top of the gold nano-structure layer. The iridium oxide layer has a spongey consistency and provides a surface modification suitable for a range of biosensing or electrochemical applications. For example, the IrOx layer facilitates pH sensing. Also, the chemical properties of iridium oxide provide increased charge storage capacity which enables current injection and amperometric analyte detection (detection of ions in a solution based on electrical current), e.g. for detecting dopamine. This can be useful for neuronal sensing and stimulation for example (stimulation refers to the stimulation of specific parts of the brain with electrical impulses delivered by a neural probe, which can be useful for treatment of neurological diseases for example).

For glass ensheathed ultramicroelectrodes (UMEs) to be used in any electrophysiological application which involves reception and transmission of electrical signal through any length, the following characteristics are advantageous:

- a controllable frequency response input representing one side usually the one in contact with the biological/and or liquid sample,
- a well-insulated and electrical conductive length/body and a low-ohmic connection on the other side, usually the connection side or back-end.
- UME connection to any microscopic and/or macroscopic conductor by mechanical means either reversibly or non-reversibly preferably features a repeatedly deformable positively protruding mass from surface.

The brain produces in 30 seconds as much electrical data as the Hubble telescope will produce in its lifetime, with the vast amount of data resulting from chemical, biochemical and electrochemical events at cellular, tissue and system levels. Understanding how the sum of these interactions result in behaviour is a major topic of interest, but current technical limitations regarding probe size, geometry, recording capability, channel number and versatility towards other types of information keep the advancement of our understanding of how the brain works at a slow pace. Glass ensheathed UMEs represent an ideal platform for brain activity mapping from both extracellular and intracellular space because of their small size, massive scalability and ability to be interfaced with emerging high-channel count read-out technologies all considered solutions to current tech bottlenecks in experimental neurosciences. UMEs feature small stray capacitances (e.g. less than 0.5 $pFcm^{-2}$) given the high insulator-conductor ratio, mechanical workability, broad material choice and commercial availability. UMEs usually have one dimension in the micrometre or nanometre domain and at least one the millimetre or centimetre region, thus the properties of the electrified interfaces are to be carefully considered when high frequency electrical signal need to be passed by micron-sized or nano-sized interfaces.

Current challenges in neural sensor miniaturisation are signal coupling and transport from the electrogenic cells trough the interfaces, on different conductor lengths towards the resistive junction to finally be delivered and processed by the read out circuitry. The smaller the sensors are, the higher impedances (Z) in aqueous electrolytes become, resulting in significantly weakened signals and high noise levels. The interface's electrical coupling properties consequently bring limitations in the design of the read-out systems. Firstly, more amplifier stages and higher amplifier gains are required to condition recorded signals. Secondly, pre-filter and impedance matching circuitry are included to reduce ambient noise and pick up small-signals. Thirdly, power consumption of these additional amplifier stages could easily be a critical issue when limited power sources are available i.e. for battery powered tethered chronic neural implants—thus improving signal strength while keeping electrode dimensions in the micron and sub-micron domain is of paramount importance.

These issues can be addressed using the electrochemical probe discussed above. By performing a two-step surface modification of the tips of the UMEs at the front end, to include both a highly fractalized flake-like gold nano-structure layer and a second layer of highly porous metal oxide (e.g. iridium oxide), the impedance at the front end of the electrodes can be greatly reduced. This is shown in the graph of FIG. 4 which compares the impedance across different frequencies for three probes:

"polished Au"—a probe made of bare gold metal wires without surface modification of the tips at the front end
"IrOx modified"—a probe where the tips of the wires at the front end have the IrOx layer but not the intervening gold nano-structure layer
"jULIE"—a probe as in the example of FIG. 1 with both the gold nano-structure layer and the IrOx layer at the front end tips of the wires.

Figure 4:
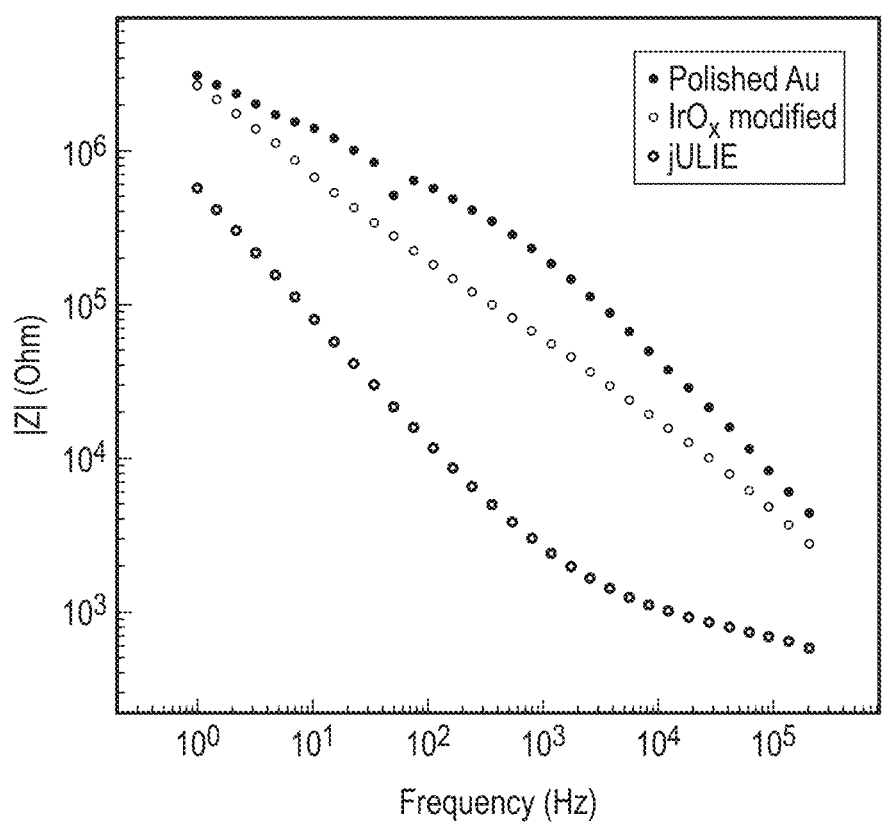
FIG. 4 is a graph showing how the impedance at the front end interface of the wires is reduced by including the layer of gold nano-structures.
Figure 5:
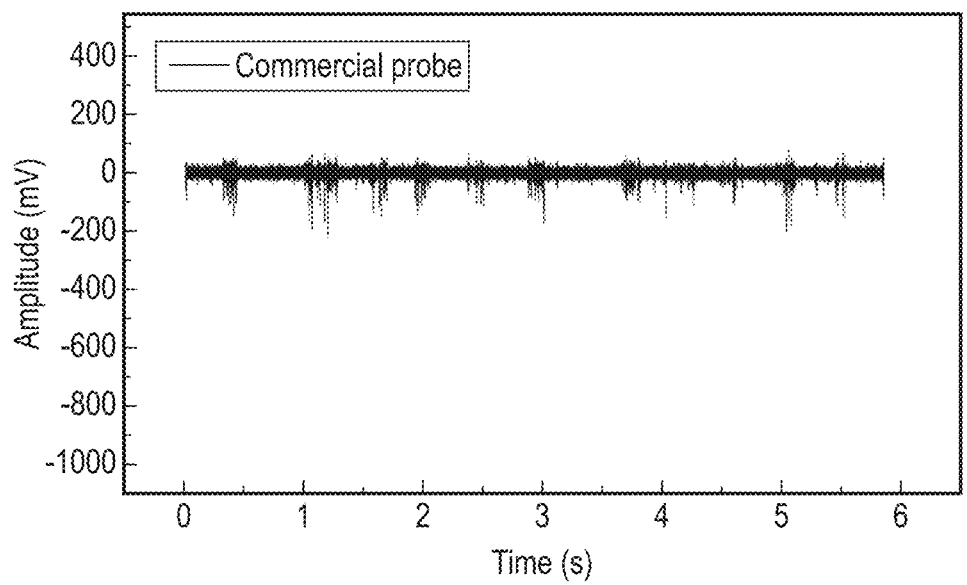
FIGS. 5 and 6 compares signal amplitudes of neuronal recordings measured in a mouse brain using a typical commercial probe and the electrochemical probe of the present technique respectively.
Figure 6:
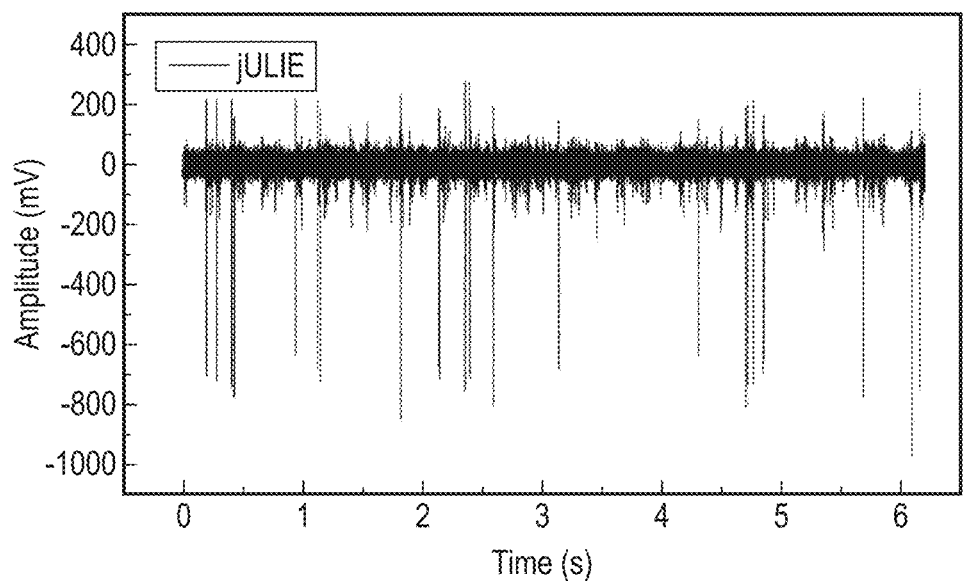

As shown in FIG. 4, the impedance at the front end of the jULIE wires is an order of magnitude lower than the other types of wires. To test jULIEs we performed recordings in the olfactory bulb (OB) of anaesthetized mice (4-6 weeks old, Ketamine/Xylazine anaesthesia) using a Tucker Davis RZ2 amplifier with a PZ2 pre-amplifier and RA16AC-Z headstage. Extracellular spikes were reliably recorded with amplitudes of up to 1.6 mV. Consistent with this, when jULIEs were lowered several mm into the brain and returned to a superficial recording position, extracellular units were reliably recorded throughout the olfactory bulb. Due to the small size of the recording site and minimal damage to the tissue, jULIEs were found to be exceptionally suited for recording large amplitude (500-1500 uV), well isolated signals from the close vicinity of neurons (20-30 um). FIGS. 5 and 6 show amplitudes of neuronal recordings made in a mouse brain using a typical commercially available probe and the jULIE probe respectively. As is clear from FIG. 6, the amplitudes recorded using the jULIE probe are much larger than the amplitudes shown in FIG. 5 for the commercial probe. Hence, signal to noise ratio can be improved and there is less need for additional amplification, helping to reduce power in battery-powered implants for example.

Other advantages of the probes include:
(i) the dimensions of the penetrating wires are 2× to 5× times smaller and recording sites can be up to 50 times smaller (e.g. 1 µm) than in conventional probes. This results in reduced tissue displacement and damage as well as in highly localized recordings with better unit separation (better identification of signals from individual neurons).
(ii) the nanostructured interface represents an excellent platform for further improved electrical coupling characteristics with the extracellular media, for example the nano-sized gold/IrOx interface allows for substantially higher signal-to-noise with amplitudes of up to 1.5 mV compared to typically 200-500 pV with conventional electrodes.
(iii) the material choice enables semi-automatic preparation for recording sites pre-arrangement to fit anatomical structures; and needle-like sharpening for seamless penetration of the neural tissue.
(iv) there are also substantially improved charge transfer capabilities i.e. enabling current injection for stimulation purposes and neurotransmitters or other analyte monitoring (e.g. alcohol, paracetamol), in a highly localized manner.

Figure 7:
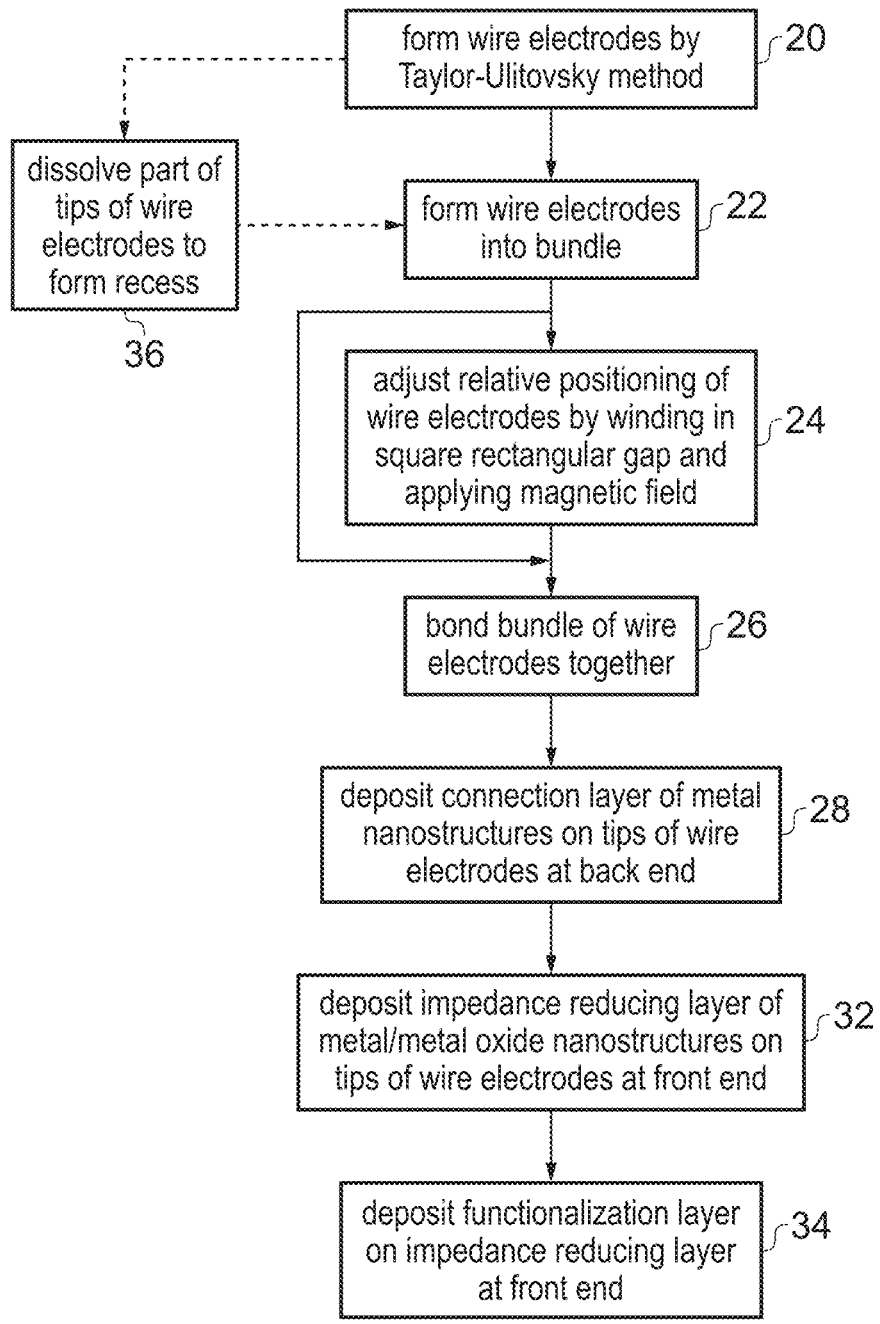
FIG. 7 is a flow diagram illustrating a method of manufacturing an electrochemical probe.

FIG. 7 is a flow diagram illustrating a method of manufacturing an electrochemical probe. At step 20 wire electrodes are formed using the Taylor-Ulitovsky method. The Taylor-Ulitovsky method is a technique for forming glass-sheathed wire electrodes with a very fine diameter, e.g. as small as a few microns. In the process, the metal or alloy conducting material is placed inside a glass tube which is closed at one end and the other end of the tube is heated to soften the glass to a temperature at which the conductor melts. The glass can then be drawn down to produce a fine glass capillary with the metal core inside the glass. Hence, metal cores of diameters in the range 1 to 120 microns can be coated with a glass sheath a few microns thick with this method. In particular, wires with a core in the range 1-10 µm surrounded in 10-40 µm of glass can be useful for electrical and electrochemical sensing. The metal used can include copper, silver, gold, iron, platinum, lead or other metals as well as crystalline or amorphous alloy compositions such as brass, bronze, platinum-iridium, or magnetic alloys.

At step 22, the electrodes are formed into a bundle or stack with the wires running parallel to each other. For example, the microwires can be machine wrapped into bundles of 10s, 100s, 1000s, or 10000s of wire electrodes, to provide multiple channels for recording or cover the available contact portions on an integrated circuit.

Figure 8:
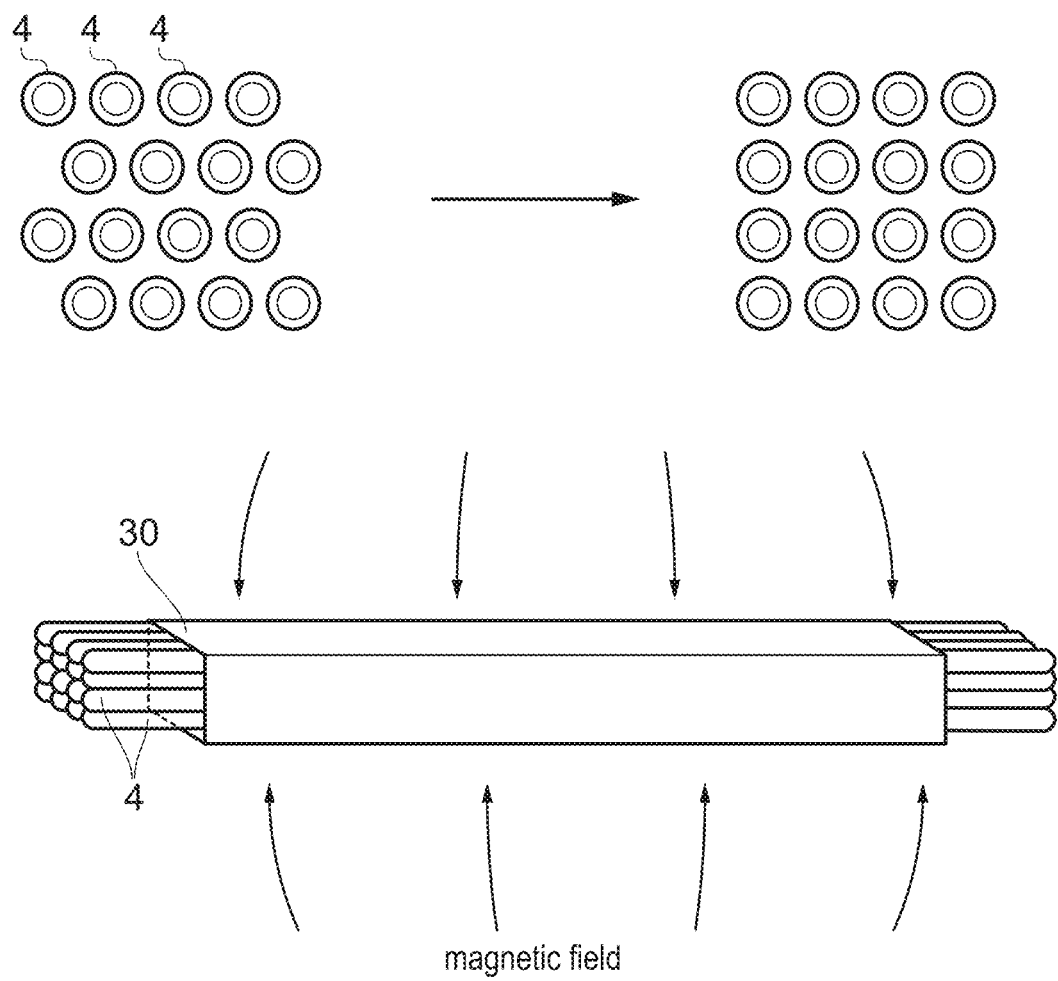
FIG. 8 schematically illustrates an example of adjusting the relative positioning of the wire electrodes in the wire bundle using a magnetic field.

At step 24, the relative positioning of the wire electrodes in the bundle is adjusted using a magnetic field, as shown schematically in FIG. 8. As shown in the top part of FIG. 8, when the wire electrodes 4 with a substantially round cross-section are bundled together they will tend to pack together in a hexagonal packed arrangement, in which the electrodes in one row are offset relative to the electrodes in another row. However, as will be discussed below, for reading out the signals measured using the electrodes, it can be useful to interface the wire electrodes with respective contact portions of an integrated circuit (IC), such as those used in multi-electrode arrays (MEA) and other pixelated integrated circuits. Most commercially available ICs have the pixelated contact portions of the readout circuits arranged in a two-dimensional square or rectangular grid pattern. Therefore, to match the industry standard rectangular contact point arrangement of an integrated circuit, it can be useful to reposition the wires in the bundle to form a square or rectangular grid pattern, in which the electrodes form rows and columns as shown in the right hand diagram at the top of FIG. 8. The lower part of FIG. 8 shows one technique by which this can be done. The wire electrodes 4 are wound through a passageway 30 having a square or rectangular cross section. For example, the passageway 30 may be a tube which could be enclosed on all four sides of the bundle, or could be missing one of the sides (e.g. winding the wires through the inside of a U-shaped bar can be enough). By applying a strong magnetic field (stronger than the electrostatics acting on the wires) to the wires as they pass through the gap, the relative positioning of the wire electrodes can be adjusted to form a square or rectangular grid array. For example, if the wires have gold cores, gold is a diamagnetic material and so a strong enough magnetic field can slightly repel the gold wires, and by pushing them up against the inside of a square or rectangular tube, this forces the wires into the desired square or rectangular grid arrangement.

Alternatively, step 24 can be omitted if the pitch of the wires within the bundle or the size of the gold contacts bumps at the back end of the wires will be sufficient that they can interface with a readout circuit regardless of the hexagonal packed arrangement.

Figure 9:
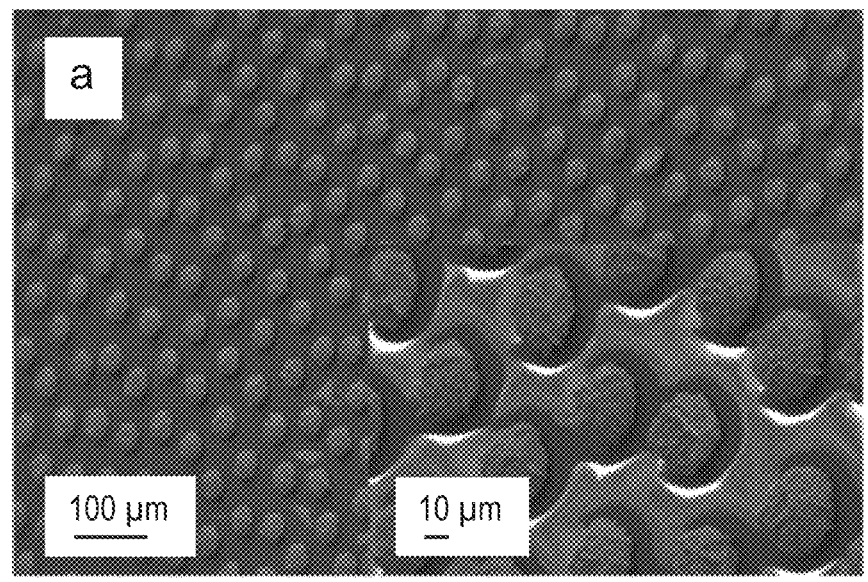
FIG. 9 is an image showing an example where the insulating sheathes of the wire electrodes are melted together to bond the wires together in the bundle.

At step 26 of FIG. 7, the bundle of wire electrodes is bonded together. This can be done in various ways. In one example, a filler material or adhesive may be introduced between the respective insulating sheets of the wire electrodes 4 to bond the electrodes together in the bundle. Alternatively, as shown in the example of FIG. 9, the wire electrodes can be bonded together by melting the insulating sheath of respective wires together so as to coalesce the insulator into a common matrix of insulating material surrounding the conducting wire electrodes. For example, this approach can be particularly useful when the insulating material is glass. Hence, as shown in the example of FIG. 9, the individual sheaths of the different wires are no longer visible and instead the wire electrodes are surrounded by a common insulating matrix of glass. This approach can be particularly useful for increasing channel density, because by avoiding the need to include a filler or adhesive between the respective wires, a greater number of electrodes per unit area can be included in the bundle.

Note that the wire electrodes do not need to be bonded along their full length. For example, it can be useful to leave a portion of the wire electrodes nearest the front end of the probe unbonded so that the free ends of the wire electrodes can spread out when inserted into a target sample, to increase the area over which recordings or current injection can be performed.

At step 28, a connection layer comprising metal nano-structures is deposited on the tips of the wire electrodes at the back end of the probe. The connection layer can be deposited by electrodeposition, in which the bundle of electrodes is held in a bath of electrolyte and a voltage difference is applied between the wire bundle and another electrode to cause ions in the electrolyte to be attracted to the wire electrode bundle, depositing a coating of metal nano-structures on the tip of each wire.

In one particular example, gold micro-hemispheres were deposited from a two-part aqueous cyanide bath containing 50 gL$^{-1}$ potassium dicyanoaureate(I) (K$_2$[Au(CN)$_2$]) and 500 gL$^{-1}$ KH$_2$PO$_4$ dissolved sequentially in deionized water (18 MOhm) (Tech, UK) at 60° C. All reagents were supplied by Sigma-Aldrich, UK, and were used without further purification. Prior to electrodeposition the polished substrate was washed with ethanol (90%), rinsed with deionized water, wiped with a lint-free cloth (Kimwipes, Kimtech, UK) and dried at 50° C. for 1 hour in an autoclave. The electrodeposition protocol was carried out with a VSP 300 potentiostat-galvanostat (Bio-Logic, France) controlled with EC-Lab (Bio-Logic, France) in a three-electrode cell setup composed of a gold UME bundle as working electrode (W$_E$), a coiled platinum wire (99.99%, GoodFellow, US) as counter electrode (CE) and a Ag/AgCl|KCl/$_{3.5M}$ reference electrode (REF) supplied by BASi, USA (E vs. NHE=0.205V). The REF was kept separated from the bath by a glass tube containing the support electrolyte and a porous Vycor glass separator. During gold deposition the W$_E$ potential was kept at E$_{red}$=−1.1V vs. REF for a time determined according to the desired size of the gold hemisphere to be formed. During electrodepostion the bath was thermostated at 60° C. under vigorous (500 rpm) stirring. This technique has been successful for many different types of metal conductor material, including gold, platinum, tin, copper, brass, bronze, silver and lead.

Figure 10:
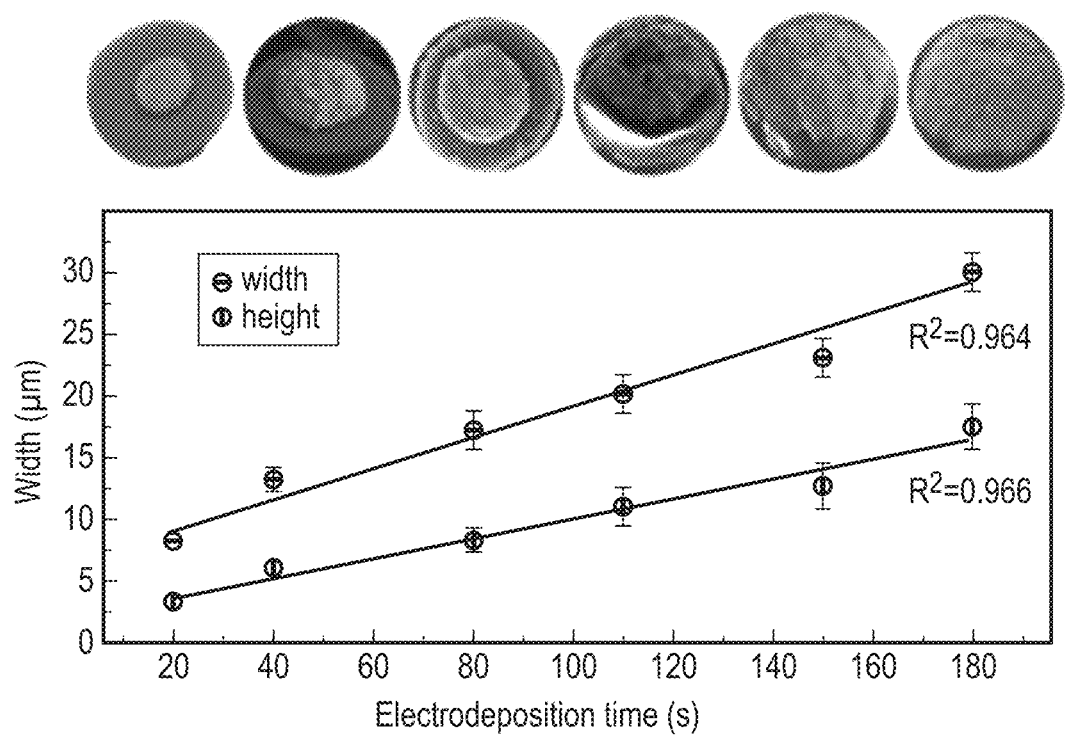
FIG. 10 is a graph showing variation of the size of gold nano-structure bumps with electrodeposition time.

FIG. 10 is a graph showing how varying the time for which the electrodeposition is performed affects the size of the gold nano-structure bumps formed on the end of the wires. The upper line in FIG. 10 shows variation of the width of the gold bumps with electrodeposition time, and the lower line shows variation of the height of the bumps with electrodeposition time. Hence, the size of the gold bumps can be carefully controlled by varying the electro-deposition time.

Gold can be a particularly useful material for the back end connection layer. In contrast with their applications for the front end sensing, the connection of individual or high-count bundled UMEs to integrated circuitry is poorly examined and represents a significant drawback towards their usability in biomedical applications. Literature offers little or no documentation regarding reversible interfacing methods of individual or UMEs to macroscopic conductors or integrated circuitry, the main practices being based on soldering, conductive silver-epoxy bonding or mercury-dip. Although applied, these methods can easily increase the RC cell time constant at high frequencies given the stray capacitance at the glass-mercury/conductive epoxy junctions and are not relevant for reversible contacting individual or bundled UME assemblies; scaling such practices to high-count UME bundles (up to 1 million, for example) are a considerable engineering challenge. The state-of-the-art indium bump bonding developed for pixelated sensor and read-out chip interconnection employing photolithography, sputtering and evaporation or later electrodeposition could be a suitable processing practice, however due to indium's tensile and ductile properties, mechanical properties and overall tribological behaviour it cannot be applied as a reversible interconnection material in UME interfacing. Copper bumps as interconnects could be considered from a mechanical point of view, however given their possible diffusion into SiO in the presence of an electric field, breaking down transistor reliability, and affinity towards oxidation, make Cu a less attractive candidate as an interconnect material in physiological environments. In contrast, gold is a promising contact material in medium wear conditions which can seamlessly enable reversible, scalable, low-cost, ultra-fine pitch and high yield bumping for interconnection purposes.

At step 32 of FIG. 7, an impedance reducing layer of metal or metal oxide nano-structures is deposited on the tips of the wire electrodes at the front end. This can be done by the same electrodeposition protocol as described above for step 28 for the back end. The material used for the nano-structures at the front end can be the same or different to the material used for the nano-structures at the back end, but in one example both use gold nano-structures.

At step 34 a functionalization layer is deposited on the impedance reducing layer at the front end. Again, this can be deposited by electrodeposition (although other techniques such as spraying could also be used). For example, a layer of metal oxide (e.g. iridium oxide) can be deposited on top of the gold nano-structures at the front end.

In one particular example, the electrodeposition protocol was carried out from a modified electrolyte solution based on a formulation reported by Meyer et al. (2001, "Electrodeposited iridium oxide for neural stimulation and recording electrodes", Neural Systems and Rehabilitation Engineering, IEEE Transactions on, 9(1), pp. 2-11.), containing 10 gL$^{-1}$ iridium (IV) chloride hydrate (99.9%, trace metal basis, Sigma-Aldrich, Germany), 25.3 gL$^{-1}$ oxalic acid dihydrate (reagent grade, Sigma-Aldrich, Germany), and 13.32 gL$^{-1}$ potassium carbonate (99.0%, BioXtra, Sigma-Aldrich, Germany). Reagents were added sequentially to 50% of the solvent's volume first by dissolving IrCl in the presence of oxalic acid followed by the addition of $K_2CO_3$ over a 16 hour period until a pH=12 was reached. The electrolyte was aged for approximately 20 days at room temperature in normal light conditions until the solution reached a dark blue colour. IrOx was electrodeposited using a multichannel VSP 300 (Bio-Logic, France) potentiostat-galvanostat in 3 electrode cell setup comprising a glass-ensheathed Au wire bundle as working electrode (WE), a platinum rod (0.5 mm diameter, 99.95%, Goodfellow, US) as counter electrode, and Ag|AgCl|KCl$/_{3.5M}$ (Bioanalytical Systems, US) as a reference electrode (REF). The electrochemical protocol was composed of three consecutive stages combining galvanostatic polarisation (GP), cyclic voltammetry (CV) and pulsed potentiostatic protocols (PP). Between protocols open circuit voltage (OCV) of the WE was monitored for 180 second and represents the steady-state period. During galvanostatic deposition the WE potential was set to 0.8V vs. REF for 500 seconds. During CV deposition the WE potential was swept from −0.5V to 0.60 V vs. REF at 100 mVs in both anodic and cathodic direction. During the pulsed potentiostatic deposition the WE potential was stepped from 0V to 0.60V vs. REF with 1 seconds steps for 500 seconds.

Figure 11:
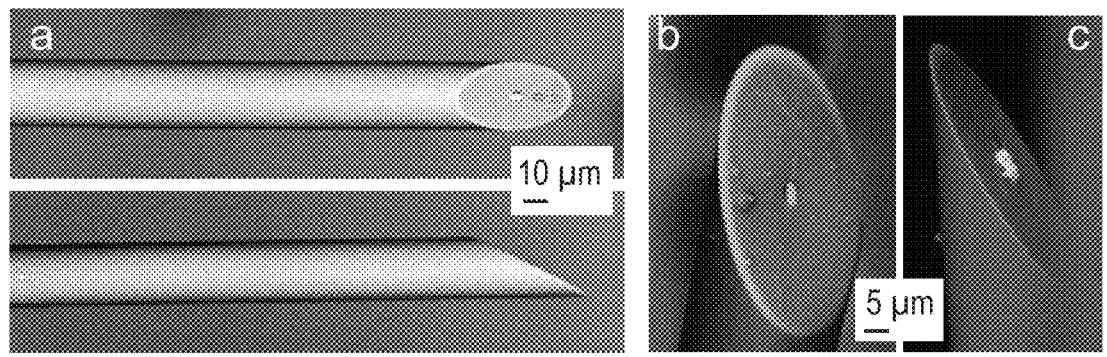
FIG. 11 shows an example of sharpened tips of the wires.

As shown in FIG. 11, the tips of the wire electrodes at the front end can be sharpened to provide a tapered surface that is angled to a point, to facilitate insertion into the brain or other sample material. Different electrodes of the bundle may have the angled surface in different orientations so that when the bundle is inserted into the sample, the angled surface pushes against the sample and is deflected sideways (towards the "pointy side" of the electrode—the side of the tip surface where the point of the tip is located—e.g. in the lower window in section a of FIG. 11 the pointy side would be the lower side of the tip surface). For example, by arranging the bundle so that the pointy side of the electrodes are arranged towards the outside of the bundle, then when the bundle is inserted into the sample the free ends of the wire electrodes can diverge and the electrodes can spread out to reach different target areas within the sample, which can be particularly useful for brain stimulation or neuronal recording for example.

Figure 12:
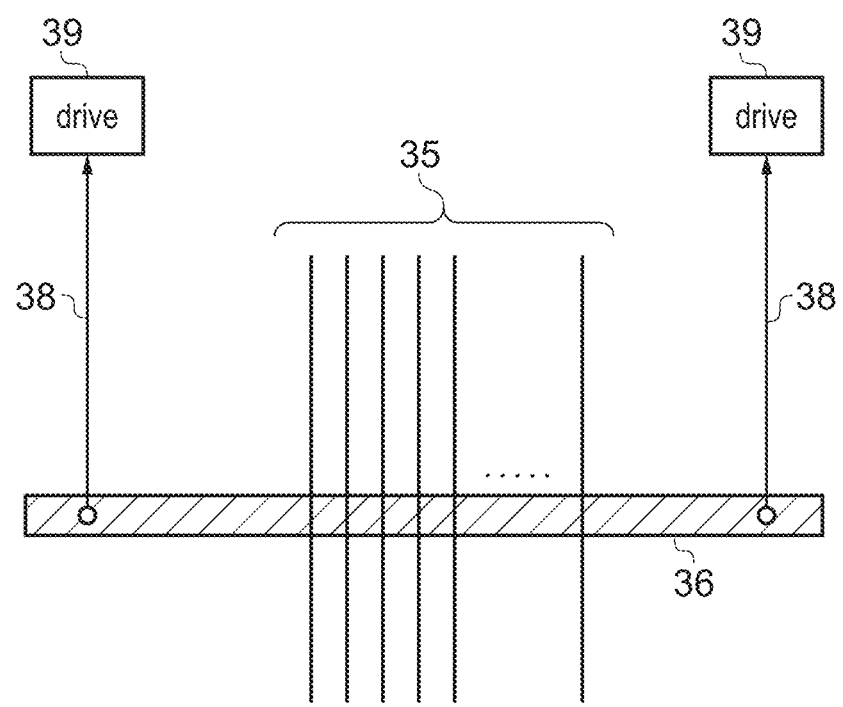
FIG. 12 shows an example in which a harness layer made of piezoelectric material is provided.

It is also possible to provide a probe with the ability to actively control the direction of the wire electrodes through the sample as it is inserted. For example, as shown in FIG. 12 the bundle 35 of wire electrodes may be disposed within a harness layer 36, along at least part of the length of the wire electrodes (it is not necessary to provide the harness layer 36 along the full length of the electrodes). The insulating material surrounding the electrodes is not shown in FIG. 12 for conciseness—this is still provided. While FIG. 12 shows an example where the wire electrodes are embedded in a continuous matrix of the harness layer 36, it is also possible to provide the harness layer 36 as a membrane or disk which extends around the outside of the wire bundle extends between the respective wires inside the bundle. For example, the disk may be placed around 30-40% of the length of the wire away from the front end of the bundle.

A number of threads 38 (e.g. made of textile) may be attached to the harness layer 36 at different points about the perimeter of the wire bundle. For example, at least three threads may be provided. Each of the threads is attached to a drive unit 39 which controls, separately for each thread, the length of thread between the harness layer 36 and the drive 39. Hence, the drive unit 39 can selectively apply a force to any given thread 38 to pull on the harness layer, thus applying bending of the bundle tip orientation. Hence, depending on which threads the force is applied to, the wire bundle can be "steered" in the desired direction to control the passage of the probe into the sample and cause the wire electrodes to reach the desired location in the sample.

Optionally, the method of FIG. 7 may include an additional recess forming step 36 between steps 20 and 22. In step 36, part of the tips of the electrode is dissolved using a solvent to form a recess 40 in the end surface of the electrode 4 as shown in part a) of FIG. 12. For example, the recess can be formed by an electrochemical leaching step (e.g. by dissolving into an electrolyte in the presence of electrical current). The parts of the electrode 4 which are not to be dissolved may be masked by covering them with a mask material, so that only the portion at the end of the tip is dissolved. The subsequent steps of FIG. 7 are then performed on the wire electrodes having the recess in their tips. Therefore, as shown in part b) of FIG. 13, when the impedance reducing layer is subsequently deposited at step 28 of FIG. 7, the nano-structures 42 are deposited on the inside of the recess 40. The nano-structures 42 may also extend onto the surface of the electrode tip outside the recess. When the functionalization layer (e.g. IrOx) is then deposited on top of the impedance reducing layer at step 34, the functionalization layer 44 is deposited inside the recess. The functionalization material may also protrude out of the recess beyond the end of the electrode tip as shown in part C of FIG. 13.

Figure 13:
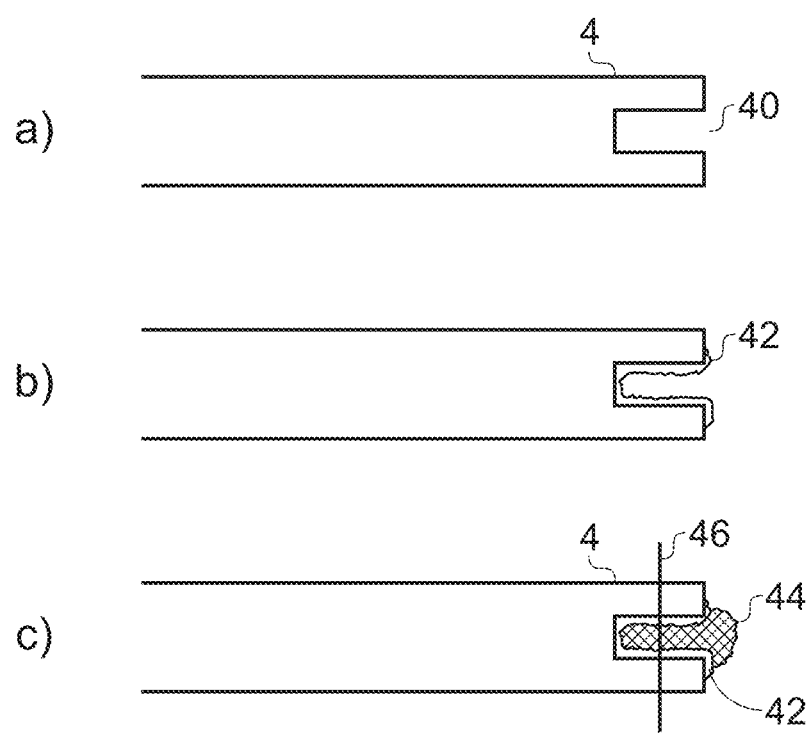
FIG. 13 shows an example where a recess is formed in the tips of the wires and the impedance reducing layer and functionalization layer are deposited on the inside of the recess.

The approach shown in FIG. 13 provides several advantages. Firstly, providing a recess means that a greater volume of iridium oxide or other functionalization material can be deposited at the end of the electrode, which can improve the electrochemical properties of the probe. For example, given the available space, the charge capacity of the iridium oxide layer can be improved up to a 1000 times. Also, this approach provides robustness against mechanical deterioration of the electrode tips. During the working life of the probe, the electrodes may repeatedly be inserted into a sample and removed, and so the tips of the electrodes may gradually be worn away by contact against the sample, which can cause deterioration of the signals measured by the probe. By including the recess and depositing the surface layers inside the recess, then even if the end of the probe is worn down (e.g. so that the surface now is at the position indicated by the line 46 in FIG. 13), then there will still be a layer of the impedance reducing nano-structures and a layer of the functionalization material at the end of the electrodes, so that the electrode can still perform its function. Therefore, the recessed design helps to increase the probe lifetime.

Figure 14:
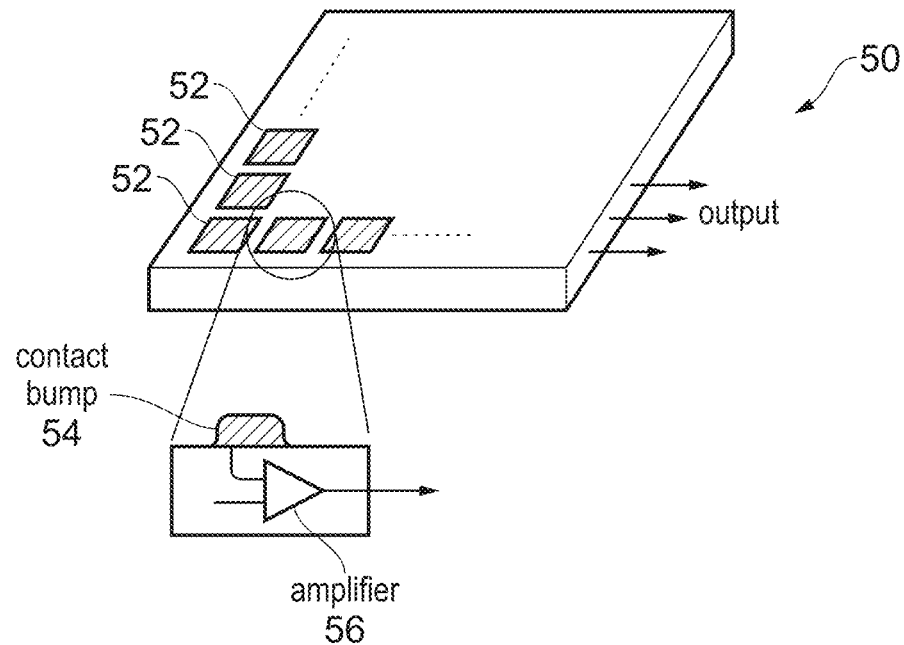
FIG. 14 shows an example of an integrated circuit.

FIG. 14 shows an example of an integrated circuit (IC) 50 which can be used to read out and amplify signals measured using the electrochemical probe. The IC 50 may be a multi electrode array (MEA), a CMOS based potentiostat or a pixelated photodetector. All these are already available commercially and therefore it is not necessary to design a bespoke circuit for this purpose, which reduces the cost of implementing an apparatus for electrochemical measurements. As shown in FIG. 14, the IC 50 includes a number of pixel read out circuits 52 arranged in a square or rectangular grid pattern, with each pixel readout circuit including a contact region 54 made from a conductive material (e.g. platinum, gold, indium) connected to an amplifier read out circuit 56. The amplifier circuit may be formed according to any known semiconductor (e.g. CMOS-based) circuit design. The signals amplified by each pixel readout circuit may then be output to a processor, memory or external apparatus for storage or analysis.

Figure 15:
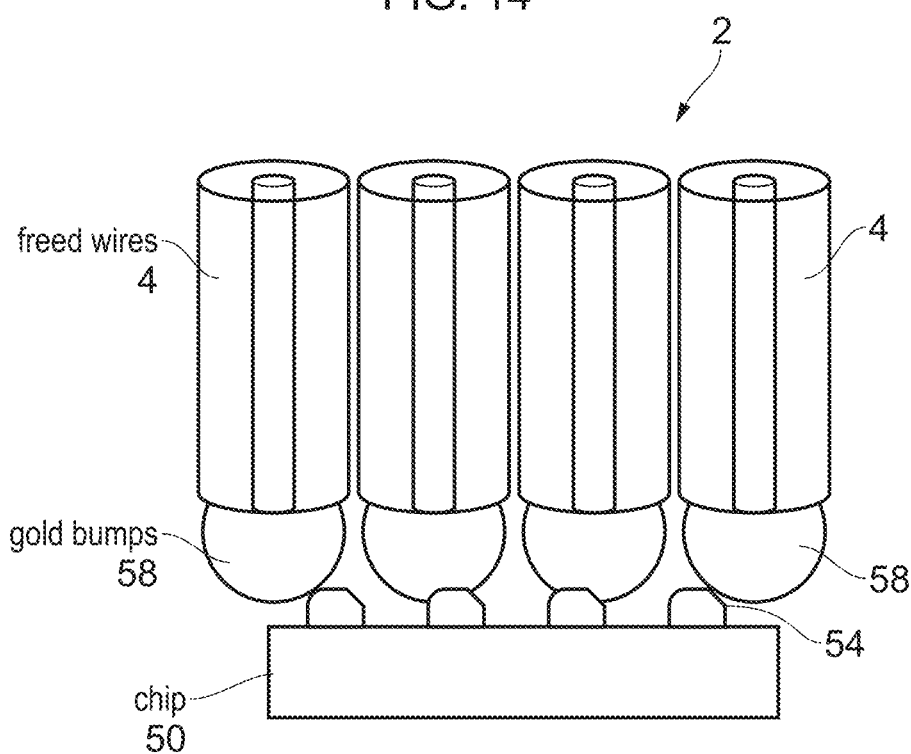
FIG. 15 shows an example of an apparatus in which the integrated circuit is used to read out and amplify the signals received from corresponding wire electrodes of the electrochemical probe.

FIG. 15 shows how the electrochemical probe 2 may be interfaced with the integrated circuit 50. As shown in FIG. 15, the gold contact bumps 58 at the back ends of the respective wire electrodes 4 can simply be pressed directly against the contact bumps 54 of the respective pixel readout circuits of the IC 50 to provide the electrical connection between the wires and corresponding pixels (without any interposing connector unit between the wire bundle and the IC 50). Hence, the integrated circuit provides a multi-channel amplification and readout system for reading the electrode signals from the respective wires. It is not essential that every pixel readout circuit of the IC 50 interfaces with a corresponding wire electrode. Depending on the arrangement of the wires within the bundle, it is possible that some pixel readout circuits may not contact a corresponding wire.

Figure 16:
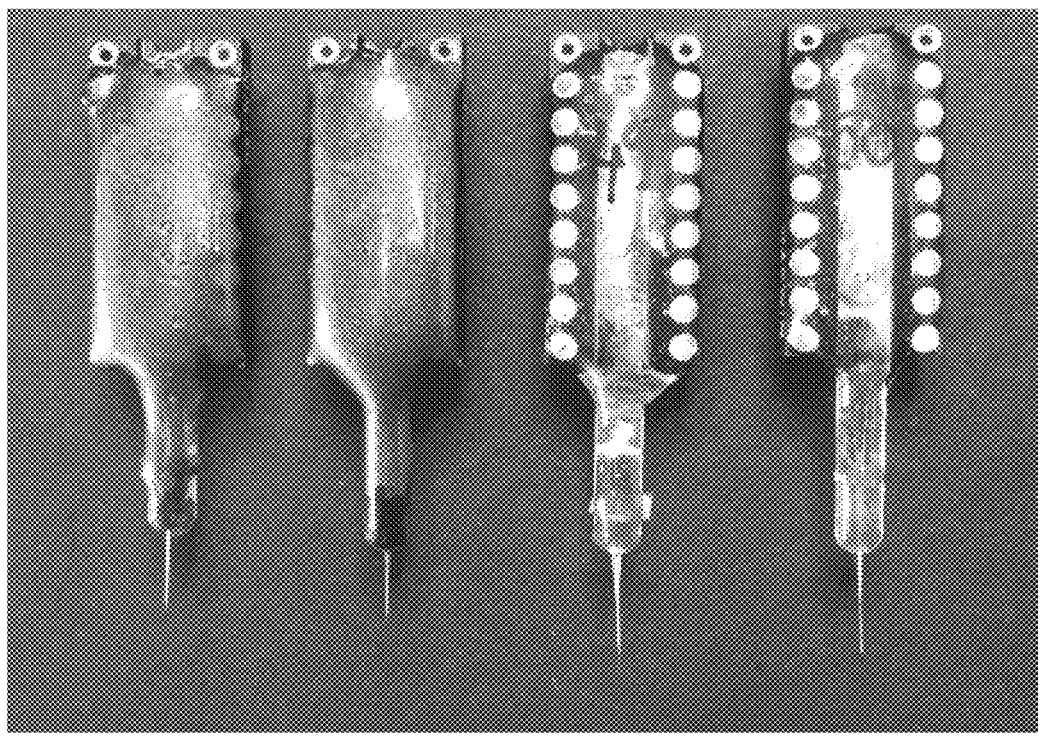
FIG. 16 is an image showing how the wires are packaged into a housing.

FIG. 16 shows an alternative technique for interfacing the probe with read out electronics or a data processing apparatus. In this example, the wire bundle forming the electrochemical probe 2 can be packaged into an enclosure, but the enclosure does not include an integrated circuit as discussed above for amplifying the signals from the probe. Instead, each wire is individually bonded or soldered to a corresponding channel of a connector (e.g. a socket or plug). When the probe is in use, the connector can be coupled to an external amplifier or other electronic device for processing the outputs of the electrodes. Hence, it is not necessary for the probe itself to include circuitry for amplifying or processing the signals read by each electrode. A free end of the wire bundle (for inserting into the sample) may extend beyond the end of the probe housing/packaging. FIG. 16 shows examples with different lengths of the free end portion of the wire electrodes, which is useful for allowing localized recordings from different regions of the sample. For example, for neuronal recording in a mouse brain, the shorter probe shown in the left hand part of FIG. 16 was used for probing the olfactory bulb while deeper structures such as the piriform-cortex were probed using the longer probes shown on the right hand side.

For wire bundles with relatively low channel count (e.g. less than 1000 wires in the bundle), either the approaches shown in FIG. 15 and FIG. 16 can be used. However, when the channel count is higher (e.g. greater than 1000 wires), then it becomes increasingly impractical to individually bond each wire to the connector, and in this case the approach shown in FIG. 15 may be more useful, whereby the bumps on the end of each wires are simply pressed against the contact portions of a pixelated integrated circuit.

In the above examples, the functionalization layer is made of iridium oxide. However, this is just one example and other types of functionalization layer could also be used. The functionalization layer may be selected according to the intended purpose of the probe. In general, the functionalization layer may be any layer for adapting the probe to a particular electrochemical application, and may be made from a range of materials. One advantage of using gold as the nano-structure impedance reducing layer is that gold nano-structures provide a good platform for a range of different functionalization layers for different biosensing or electrophysiological purposes. For example, the functionalization layer may include other metal oxides such as titanium dioxide, manganese oxides, carbon nanotubes, graphene, ATP, DNA, proteins etc.

It is also possible to provide an electrochemical probe which does not comprise any functionalization layer (i.e. step 34 of the method of FIG. 7 may be omitted). This can then provide a platform on which a downstream user of the probe can add the desired functionalization layer themselves. This approach can be useful for supporting other surface functional modifications using materials which may degrade over time and so need to be applied shortly before their use (e.g. DNA or RNA probes may be provided on the gold nanostructure impedance reducing layer, for DNA sensing).

Hence, by providing different functionalization layers, the probe may function as a wide variety of electroceutical devices (devices which employ electrical stimulation to affect or modify functions of the body) or instruments for recording data about electrical or electrochemical properties of the sample in which the probe is inserted. In some examples, the probe may have a dual function, acting as both an electroceutical device and a recording instrument. Some example applications for the probe include: neural probe; neural stimulation; cancer therapy; drug delivery; neurotransmitter detection; electrotherapy or rehabilitation; scanning electrochemical microscopy (with the probe providing multiple channels of detection in parallel); label-free affinity impedimetric biosensing (capacitance and resistance measuring); DNA sensor; pH sensor; immunosensor; glucose sensor; metal sensor; or point of care platform.

Figure 17:
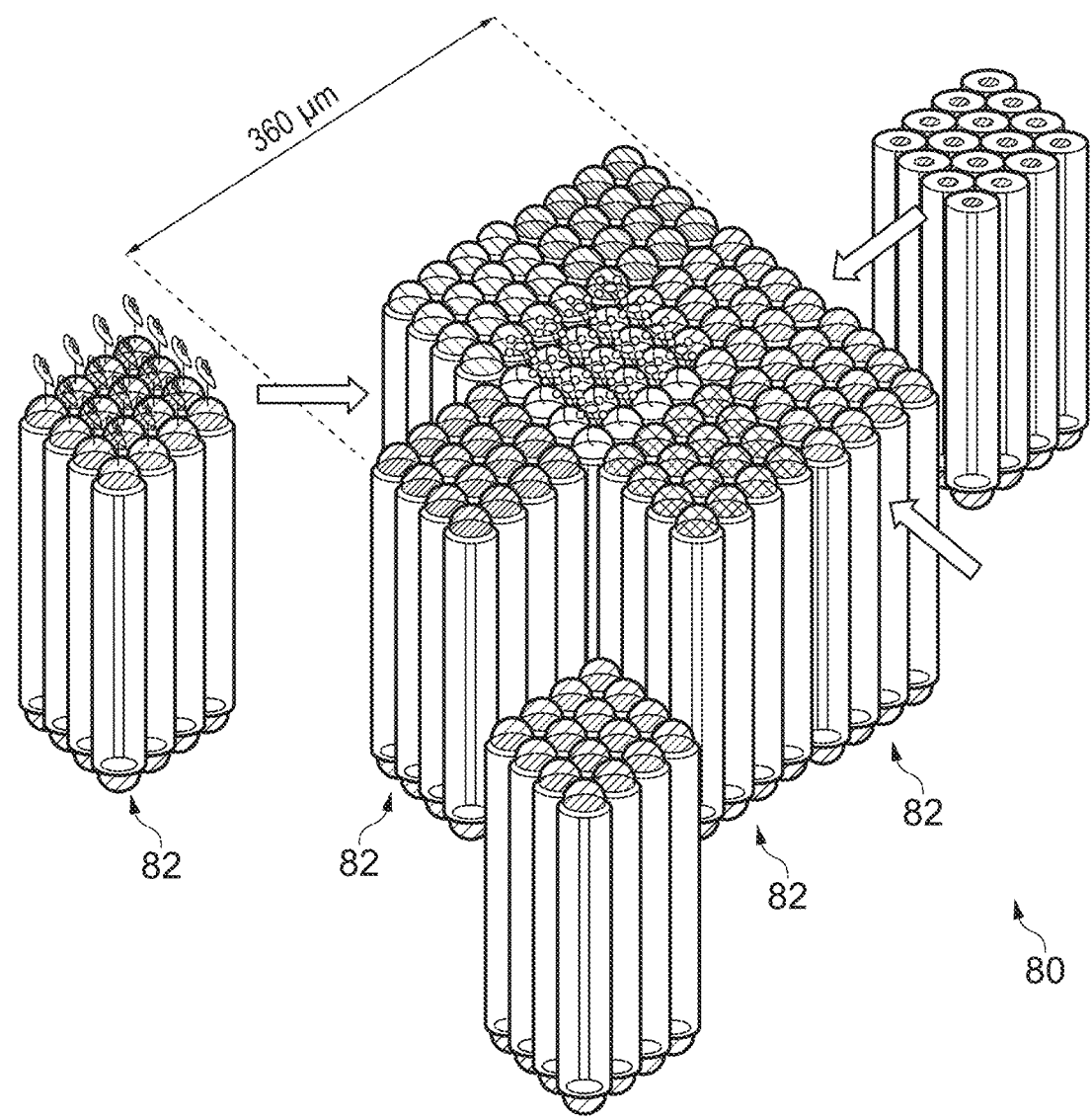
FIG. 17 shows an example of a probe comprising subsets of wire electrodes with different types of functionalization layer deposited on the impedance reducing layer.

As shown in FIG. 17, an electrochemical probe 80 may be formed where different subsets 82 of wire electrodes have different types of functionalization layer deposited on the top of the gold nano-structure impedance reducing layer at the front end of the wires. In the example shown in FIG. 17, a number of bundles may be manufactured separately using the process described above, each having a different type of functionalization layer, and then the respective bundles 82 can be assembled into a probe, to allow a single probe 80 to make two or more different types of electrochemical measurements. For example, a bundle may be provided with iridium oxide functionalization layer may sense pH or electrical currents, another bundle may have DNA probes attached for DNA sensing, and a further bundle may have a layer modified with alcohol oxidase for alcohol detection. Again, the bonding of the different subsets of wire electrodes could be done through an adhesive or a filler layer, or by melting the glass insulating sheaths of the wires together.

In another alternative, instead of forming the respective bundles 82 separately and then assembling them together, a single wire bundle could be made with different functionalization layers on respective wires of the bundle, for example by masking some wires during the step of depositing the functionalization layer or by ensuring that the electrodeposition current is only applied to some of the wires, with multiple functionalization deposition steps for the different types of functionalization layer.

Figure 18:
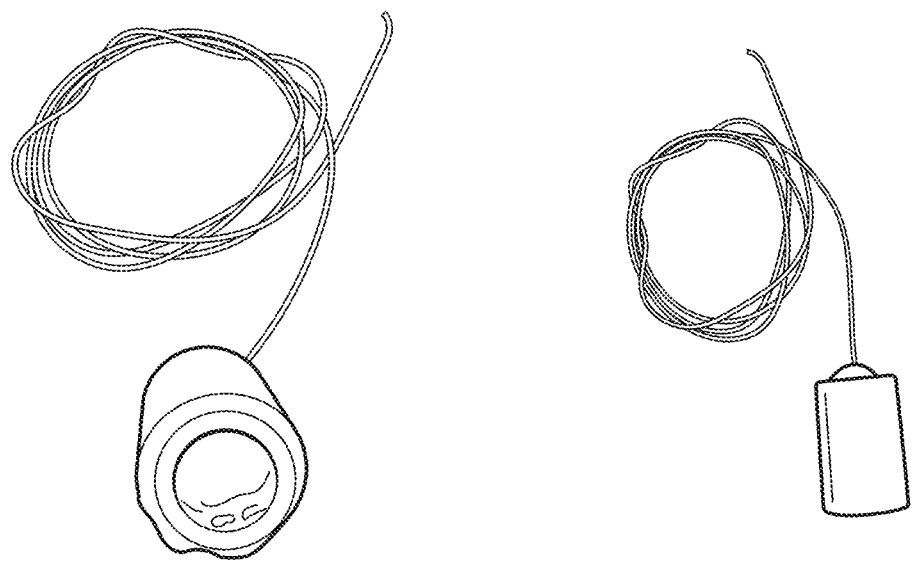
FIG. 18 shows a connector interface for coupling the wire bundle to a conductive wire, which can be used during the steps of depositing the impedance reducing layer and functionalization layer.
Figure 18:
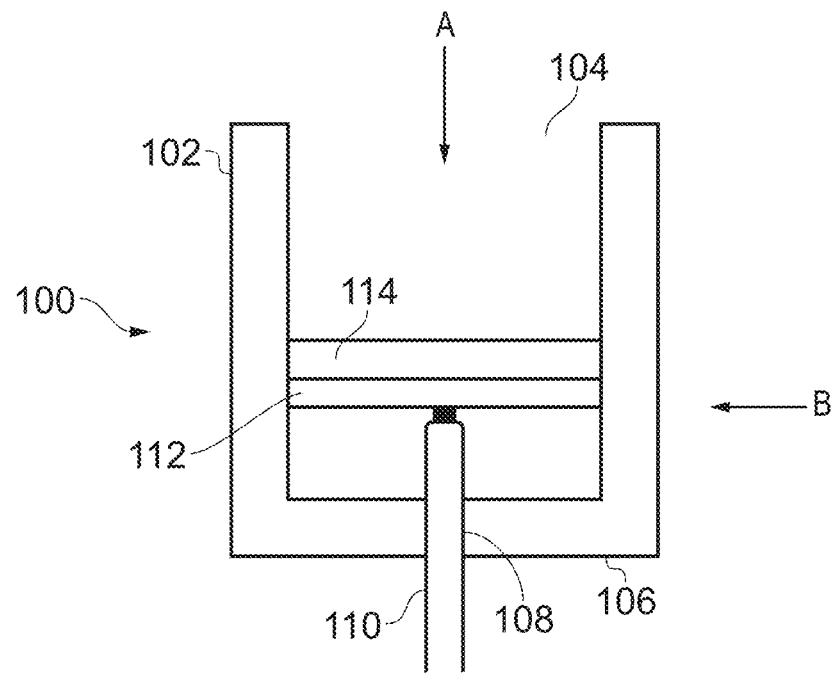

FIG. 18 shows an example of a connector interface for coupling a conductive wire to the wire bundle, which can be used during the manufacturing process of FIG. 7 for performing the electrodeposition steps 28, 32, 34 when manufacturing a probe where the channel count is too high to make it practical to individually wire up each channel in the wire bundle. The connector interface 100 is shown schematically at the bottom of FIG. 18, and the left and right images at the top of FIG. 18 show photographs of the connector interface 100 when viewed along directions A and B respectively. As shown in the schematic diagram, the connector interface 100 includes a casing 102. In this example, the casing is cylindrical, but it could also be other shapes. The casing has an open end comprising an aperture 104 for receiving the wire bundle. The diameter of the aperture is designed to correspond with the diameter of the wire bundle and any embedding material. The other end of the casing 104 is substantially closed, except for a smaller hole 108 through which an insulated conductive wire 110 is inserted. A conductive layer (e.g. a metal disk in this example) is disposed within the casing, and the end of the conductive wire is bonded to the conductive layer 112, e.g. by soldering. The insulating sheath of the conductive wire 110 can be glued into the hole 108 in the back surface of the casing 106 to prevent the conductive wire being removed. A second layer 114 is disposed on the other side of the conductive layer 112 from the side connected to the wire 108. The second layer 114 is formed of a carbon composite material. For example, the composite layer 114 may be a disk or blob made of a composite of nanocarbon, mineral oil and an ionic liquid.

During the manufacturing process, during the electrode-position steps, the wire bundle can be inserted into the open end of the connector interface casing 102 and pressed against the carbon composite layer 114 until a snug fit is obtained. The free end of the conductive wire 110 can be connected to the potentiostat or other apparatus for performing the deposition process. Since for high channel count probes, there is no adequate electronics to handle electrode-postion of so many wires, by the use of the carbon composite we shorten all the wires together and apply identical electrical parameters to all of them simultaneously—so essentially the whole bundle acts like a single conductor. Using such a connector interface 100 provides several advantages. The carbon composite layer 114 provides a non-deforming, washable, cheap, non-toxic and reversible connection method for working both ends of the wire bundle. This is particularly useful when depositing the functionalization layer at step 34 of FIG. 7, because at this point the wires in the bundle already have the metal or metal oxide hemispheres deposited on them, and it can be important to avoid deforming these hemispheres when connecting the wires to the electrodeposition apparatus for depositing the functionalization layer.

In summary, by providing an electrochemical probe comprising a wire bundle comprising a number of wire electrodes made of conducting material bundled parallel to each other and insulating material surrounded the electrodes, with an impedance reducing layer of metal or metal oxide nano-structures deposited on the tips of the wire electrodes at the first end of the wire bundle and a functionalization layer deposited on the impedance reducing layer at the first end, this can provide an electrochemical probe with much lower impedance at that front end, increasing the amplitude of electrochemical signals measured using the probe or of currents transmitted by the probe for stimulation purposes. This can be useful for a range of applications including neuronal recording, brain mapping or stimulation monitoring of spinal cord lesions, cardiovascular function monitoring, tumor electrotherapy, toxicological interrogation and many other biomedical or electrophysiological applications. The core material may be one of gold, platinum, copper, brass, nickel, tin, silver, iron, lead, brass, bronze, platinum-iridium, silver-lead for example. The insulating material may be glass or plastic, for example.

In some examples the wire electrodes may have separate insulating sheaths of the insulating material. Alternatively, the wire electrodes may be disposed in a common insulating matrix of insulating material, which can be formed for example by melting the glass sheaths of the individual wire electrodes together as discussed above.

The metal or metal oxide used for the nano-structures in the impedance reducing layer could be any of the following: gold, platinum, ruthenium, titanium, iridium, indium, manganese, or oxides of such materials such as manganese oxide or ruthenium oxide. In particular, using nano-structures made of a noble metal, such as gold or platinum, can be particularly useful for reducing the impedance. In particular, gold nano-structures have been found to be particularly effective as shown in the graph of FIG. 4.

At a second end of the wire bundle opposite the first end, there may be a connection layer of metal nano-structures on tips of the wire electrodes. This end is used as the back end of the probe for outputting signals to readout electronics. The nanostructures in the connection layer at the second end of the wire bundle may be made of the same material as the nanostructures in the impedance reducing layer at the first end, or alternatively the respective ends of the wire bundles may be provided with nanostructures of different materials (e.g. gold at the front end of the probe and platinum at the back end). One or both of the layers of nano-structures formed at the first and second ends of the wires may be formed from separate bumps of nano-structures, with each bump formed on the tip of a respective wire electrode. The bumps may have a rounded or hemispherical profile.

In one example, the wire electrodes may be ultramicroelectrodes (UMEs). The wire electrodes may have a diameter less than or equal to 25 µm. In other examples, the wire electrodes may be even narrower, for example with a diameter less than or equal to 20 µm, less than or equal to 15 µm, less than or equal to 10 µm or less than or equal to 5 µm.

The nanostructures in the respective layers at each end of the probe may have a unit width less than or equal to 500 nm. More particularly, the unit width may be less than or equal to 400 nm, less than or equal to 300 nm, less than or equal to 200 nm, less than or equal to 100 nm or less than or equal to 50 nm. The term "unit width" refers to the width across the longest dimension of an individual nano-structure (e.g. an individual flake, grain or nanoparticle), not the width of the mass of nano-structures as a whole. In some cases the nano-structures at the first end may have a unit width which is less than or equal to 20% of the wire diameter of the electrodes, less than or equal to 15% percent of the wire diameter, less than or equal to 10% of the wire diameter, or less than or equal to 5% of the wire diameter. The nano-structures at the second end can also be less wide than the wire diameters of the electrodes, or alternatively can cover a greater area of the tips of the wire electrodes, and could cover the entire tip. Note that the different nano-structures within the layer will in practice have different unit widths to each other, but all the nano-structures may have a unit width defined within the thresholds described above. Similarly, the functionalization layer may also comprise a layer of nano-structures (e.g. of Iridium oxide, or another material), which may have unit widths as defined within the thresholds described above. The nano-structures in the functionalization layer may be of a different size to the nano-structures in the impedance reducing layer or connection layer.

The tips of the wires may be sharpened, or have a tapered end which meets at a point, to facilitate insertion into the sample.

For at least one of the wire electrodes, the tip of the electrode at the first end may comprise a recess, the impedance reducing layer may be deposited on the inside of the recess, with the functionalization layer on top of the impedance reducing layer inside the recess. The functionalization layer may protrude out of the recess.

The wire bundle may in some examples comprise a first subset of wire electrodes with a first type of functionalization layer deposited on the impedance reducing layer at said first end of the bundle, and a second subset of wire electrodes with a second type of functionalization layer deposited on the impedance reducing layer at said first end of the bundle. In some cases there may be three or more subsets of wire electrodes with different types of functionalization layer.

In the present application, the words "configured to . . ." are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

We claim:

1. An electrochemical probe comprising:
    a wire bundle comprising a plurality of wire electrodes arranged alongside each other;
    each of the plurality of wire electrodes comprising conducting material and insulating material surrounding the conducting material; and
    an impedance reducing layer of metal nano-structures or metal oxide nano-structures deposited on a polished surface of tips of the plurality of wire electrodes at a first end of the wire bundle, wherein the metal nano-structures or the metal oxide nano-structures have a unit width less than or equal to 500 nm; and
    a functionalization layer deposited on the impedance reducing layer at said first end of the wire bundle; wherein:
    along sides of the plurality of wire electrodes, said insulating material contacts the conducting material without an intervening layer of the metal nano-structures or metal oxide nano-structures; and
    for each of the plurality of wire electrodes:
        a diameter of the wire electrode is less than or equal to 25 μm;
        the first end of the wire electrode is tapered to meet at a point; and,
        the impedance reducing layer does not extend beyond the diameter of the wire electrode.

2. The electrochemical probe according to claim 1, wherein each wire electrode has a separate insulating sheath of the insulating material.

3. The electrochemical probe according to claim 1, wherein the plurality of wire electrodes are disposed in a common insulating matrix of the insulating material.

4. The electrochemical probe according to claim 1, wherein the impedance reducing layer comprises said metal nano-structures, and said metal nano-structures are made of a noble metal.

5. The electrochemical probe according to claim 1, wherein the impedance reducing layer comprises said metal nano-structures, and said metal nano-structures are gold nano-structures.

6. The electrochemical probe according to claim 1, wherein for at least one of the plurality of wire electrodes, the tip of the electrode at the first end comprises a recess, the impedance reducing layer is deposited on the inside of the recess and the functionalization layer is deposited on the impedance reducing layer inside the recess.

7. The electrochemical probe according to claim 1, wherein the wire bundle comprises:
    a first subset of the plurality of wire electrodes with a first functionalization layer deposited on the impedance reducing layer at said first end of the wire bundle; and
    a second subset of the plurality of wire electrodes with a second functionalization layer deposited on the impedance reducing layer at said first end of the wire bundle, where said second functionalization layer is different to said first functionalization layer.

8. The electrochemical probe according to claim 1, wherein the wire bundle is disposed within a harness layer, and the electrochemical probe comprises a drive configured to apply a force to one or more selected threads of a plurality of threads attached to the harness layer to control an orientation of the tip of the wire bundle at the first end.

9. The electrochemical probe of claim 1, wherein the impedance reducing layer is deposited on the tips of the wire electrodes at the first end of the wire bundle after the insulating material is already provided around the conducting material and the plurality of wire electrodes are already formed into the wire bundle.

10. An apparatus comprising:
    an electrochemical probe according to claim 1; and
    an integrated circuit comprising a plurality of contact portions to receive an electrode signal, and an amplifying portion to amplify the electrode signal received at the contact portions;
    wherein connection layers of metal nano-structures on the tips of the plurality of wire electrodes at a second end of the wire bundle opposite the first end are in contact with corresponding contact portions of the integrated circuit.

11. A method of manufacturing an electrochemical probe, comprising:
    forming a wire bundle comprising a plurality of wire electrodes arranged alongside each other, each of the plurality of wire electrodes comprising conducting material and insulating material surrounding the conducting material; and
    after the insulating material is already provided around the conducting material and the plurality of wire electrodes are already formed into said wire bundle, depositing an impedance reducing layer of metal nano-structures or metal oxide nano-structures on tips of the plurality of wire electrodes at a first end of the wire bundle; and
    depositing a functionalization layer on the impedance reducing layer at said first end of the wire bundle;
    wherein the metal nano-structures or the metal oxide nano-structures have a unit width less than or equal to 500 nm;
    along sides of the wire electrodes, said insulating material contacts the conducting material without an intervening layer of the metal nano-structures or metal oxide nano-structures; and
    for each of the plurality of wire electrodes:
        a diameter of the wire electrode is less than or equal to 25 μm;
        the first end of the wire electrode is tapered to meet at a point; and,
        the impedance reducing layer does not extend beyond the diameter of the wire electrode.

12. The method of claim 11, wherein at least one of the impedance reducing layer and the functionalization layer is formed by electrodeposition.

13. The method of claim 11, further comprising depositing a connection layer of metal nano-structures on tips of the plurality of wire electrodes at a second end of the wire bundle opposite the first end.

14. The method of claim 11, further comprising winding the plurality of wire electrodes inside a passageway having a square or rectangular cross-section, and applying a magnetic field to adjust the relative positioning of the plurality of wire electrodes in the wire bundle.

15. The method of claim 11, wherein each of the plurality of wire electrodes is separately formed with a respective sheath of insulating material before combining the plurality of wire electrodes to form the wire bundle; and
  the method further comprises melting the respective sheathes of the each of plurality of wire electrodes together to bond the plurality of wire electrodes together in the wire bundle.

16. The method of claim 11, comprising dissolving part of the tip of at least one of the plurality of wire electrodes at the first end of the wire bundle form a recess, wherein the impedance reducing layer is deposited on the inside of the recess.

17. An electrochemical probe comprising:
  a wire bundle comprising a plurality of wire electrodes arranged alongside each other,
  each of the plurality of wire electrodes comprising conducting material and insulating material surrounding the conducting material; and
  an impedance reducing layer of gold nano-structures deposited on a polished surface of tips of the plurality of wire electrodes at a first end of the wire bundle, wherein
  the gold nano-structures have a unit width less than or equal to 500 nm; and
  along sides of the plurality of wire electrodes, said insulating material contacts the conducting material without an intervening layer of the gold nano-structures; and
  for each of the plurality of wire electrodes:
    a diameter of the wire electrode is less than or equal to 25 µm;
    the first end of the wire electrode is tapered to meet at a point; and
    the impedance reducing layer does not extend beyond the diameter of the wire electrode.

* * * * *